(12) United States Patent
Ahn (10) Patent No.: US 10,172,601 B2
(45) Date of Patent: Jan. 8, 2019

(54) SPINE RETRACTOR

(71) Applicant: University Hospitals Cleveland Medical Center, Cleveland, OH (US)

(72) Inventor: Nicholas Utchan Ahn, Shaker Heights, OH (US)

(73) Assignee: UNIVERSITY HOSPITALS CLEVELAND MEDICAL CENTER, Cleveland, OH (US)

(*) Notice: Subject to any disclaimer, the term of this patent is extended or adjusted under 35 U.S.C. 154(b) by 593 days.

(21) Appl. No.: 14/692,876

(22) Filed: Apr. 22, 2015

(65) Prior Publication Data

US 2015/0297208 A1 Oct. 22, 2015

Related U.S. Application Data

(60) Provisional application No. 61/982,428, filed on Apr. 22, 2014.

(51) Int. Cl.
| | |
|---|---|
| *A61B 17/02* | (2006.01) |
| *A61B 17/17* | (2006.01) |
| *A61B 17/70* | (2006.01) |
| *A61B 17/00* | (2006.01) |

(52) U.S. Cl.
CPC .......... *A61B 17/02* (2013.01); *A61B 17/1757* (2013.01); *A61B 17/7077* (2013.01); *A61B 2017/00477* (2013.01); *A61B 2017/00526* (2013.01); *A61B 2017/0256* (2013.01)

(58) Field of Classification Search
CPC ............. A61B 17/02–17/0293; A61B 17/8883

USPC .................................................. 600/205, 221
See application file for complete search history.

(56) References Cited

U.S. PATENT DOCUMENTS

| | | | | |
|---|---|---|---|---|
| 1,706,500 | A * | 3/1929 | Smith | A61B 17/02 600/232 |
| 2,756,742 | A * | 7/1956 | Barton | A61B 1/24 128/200.26 |
| 4,156,424 | A * | 5/1979 | Burgin | A61B 1/32 600/212 |
| 4,344,419 | A * | 8/1982 | Burgin | A61B 1/24 600/212 |
| 4,562,832 | A * | 1/1986 | Wilder | A61B 1/32 138/DIG. 8 |
| 5,139,499 | A * | 8/1992 | Small | A61B 17/864 606/104 |
| 5,928,139 | A * | 7/1999 | Koros | A61B 17/0206 600/205 |
| 5,944,658 | A * | 8/1999 | Koros | A61B 17/0206 600/231 |
| 6,083,154 | A * | 7/2000 | Liu | A61B 17/0293 600/231 |

(Continued)

*Primary Examiner* — Zade Coley
(74) *Attorney, Agent, or Firm* — Pearne & Gordon LLP (57) ABSTRACT

A spinal retractor system is provided to protect important structures of a patient while the surgeon performs surgery on spinal elements of the patient. The system includes a retractor blade including a retractor tab, a side body, and an upper platform having a tool connector tab for mating with a matching blade holder tool for securely holding the retractor blade. The retractor blade also has a screw holder attached to the side body of the retractor blade for receiving a bone screw provided in a channel of the screw holder A screwdriver is used to drive the bone screw into a vertebra of a patient, such as during an anterior spinal surgical procedure.

16 Claims, 7 Drawing Sheets

(56) References Cited

U.S. PATENT DOCUMENTS

| | | | | |
|---|---|---|---|---|
| 6,206,826 B1 * | 3/2001 | Mathews | ............. | A61B 17/025 |
| | | | | 600/210 |
| 7,150,714 B2 * | 12/2006 | Myles | ................ | A61B 17/0293 |
| | | | | 600/205 |
| 9,622,795 B2 * | 4/2017 | Reitblat | ............. | A61B 17/7077 |
| 2002/0017170 A1 * | 2/2002 | Amis | ................... | F16B 23/003 |
| | | | | 81/121.1 |
| 2011/0257478 A1 * | 10/2011 | Kleiner | ................ | A61B 1/0607 |
| | | | | 600/104 |
| 2012/0271120 A1 * | 10/2012 | Seex | ...................... | A61B 17/02 |
| | | | | 600/235 |
| 2017/0325674 A1 * | 11/2017 | Kleiner | ............. | A61B 1/00154 |

\* cited by examiner

SPINE RETRACTOR

CROSS-REFERENCES TO RELATED APPLICATIONS

This application claims the benefit of U.S. provisional patent application Ser. No. 61/982,428 filed on Apr. 22, 2014, and incorporated herein by reference.

BACKGROUND

Spinal retractors are used by surgeons to protect important and fragile structures during surgery on spinal elements. However, current solutions have shortcomings that can be addressed in a new spinal retractor solution.

SUMMARY

Provided are a plurality of example embodiments, including, but not limited to, a spine retractor blade comprising: a side body; a retractor tab provided at an angle at one end of the side body; an upper platform provided at another end of the side body, the upper platform being provided substantially perpendicular to the side body; a tool connector tab provided on a surface of the upper platform, the tool connector tab being configured to be received by a blade holder tool such that the blade holder tool securely holds the retractor blade when receiving the connector tab; and a screw holder provided on a surface of the side body, the screw holder having a channel therethrough to receive a bone screw therethrough.

In the above spine retractor blade, the retractor tab can be angled away from the screw holder.

Further provided is a spine retractor system comprising: a bone screw having a threaded end and a head end; a screwdriver having a handle and a tip at an end of the screwdriver away from the handle, the tip being configured to receive the head end of the bone screw such that the screwdriver is configured to manually drive the bone screw into bone; a blade holder tool having a handle and a tool end away from the handle; and retractor blade, such as provided herein.

An example retractor blade can include: a side body, a retractor tab provided at an angle at one end of the side body, an upper platform provided at another end of the side body, the upper platform being provided at an angle to the side body, a tool connector tab provided on a surface of the upper platform, the tool connector tab being configured to be received by the tool end of the blade holder tool such that the blade holder tool securely holds the retractor blade when the tool end receives the connector tab, and a screw holder provided on a surface of the side body, the screw holder having a channel therethrough to receive the bone screw therethrough.

Another example retractor blade can include: a side body, a retractor tab provided at an angle at one end of the side body, an upper platform provided at another end of the side body, the upper platform being provided substantially perpendicular to the side body, a tool connector tab provided on a surface of the upper platform, the tool connector tab extending from the upper platform and being configured to be received by the tool end of the blade holder tool such that the blade holder tool securely holds the retractor blade when the tool end receives the connector tab, wherein the side body, the upper platform, and the retractor tab are formed from a single piece of material with a smoothly finished surface, and a substantially cylindrical screw holder provided on a surface of the side body, the screw holder having a channel therethrough to receive the bone screw therethrough, wherein the retractor tab is angled away from the screw holder.

Also included is a spine retractor system wherein the retractor system is configured to be inserted into an incision in a patient to manually drive the bone screw provided in the channel of the retractor blade into bone while the retractor blade is manually held in place by the blade holder.

Also provided is a spine retractor blade such as provided herein wherein the side body, the upper platform, and the retractor tab are formed from a single piece of material.

Also provided is a spine retractor blade such as provided herein wherein the tool connector tab is a cylindrical protrusion having a hollow center.

Also provided is a spine retractor blade such as provided herein wherein the screw holder is substantially cylindrical and mounted parallel to an axis of the hollow center of the tool connector tab.

Also provided is a spine retractor blade such as provided herein wherein the retractor tab transitions from the side body as a continuous curve.

Further provided is a method of using a spine retractor system, comprising the steps of:

providing a retractor blade such as provided herein;

mating the tool connector tab of the retractor blade with a corresponding portion of a blade holder tool;

manually inserting the retractor blade into an incision in a patient using the blade holder tool;

inserting a bone screw into the channel of the screw holder;

driving the bone screw into a portion of a vertebra of the patient using a screwdriver configured to manually drive the bone screw into the vertebra while holding the retractor blade in place using the blade holder tool; and removing the retractor blade by unscrewing the bone screw and removing the retractor blade from the incision using the blade holder tool.

Further provided are any of these methods further comprising the step of filling a hole formed by the driving step with bone wax.

Also provided are any of these methods wherein the bone wax is obtained from the bone screw.

Further provided are any of these methods wherein the method is performed as part of an anterior spinal surgical procedure.

Also provided are additional example embodiments, some, but not all of which, are described hereinbelow in more detail.

BRIEF DESCRIPTION OF THE DRAWINGS

The features and advantages of the example embodiments described herein will become apparent to those skilled in the art to which this disclosure relates upon reading the following description, with reference to the accompanying drawings, in which.

DETAILED DESCRIPTION OF THE EXAMPLE EMBODIMENTS

A retractor system is provided to protect important structures of a patient while the surgeon performs surgery on spinal elements of the patient.

Figure 6:
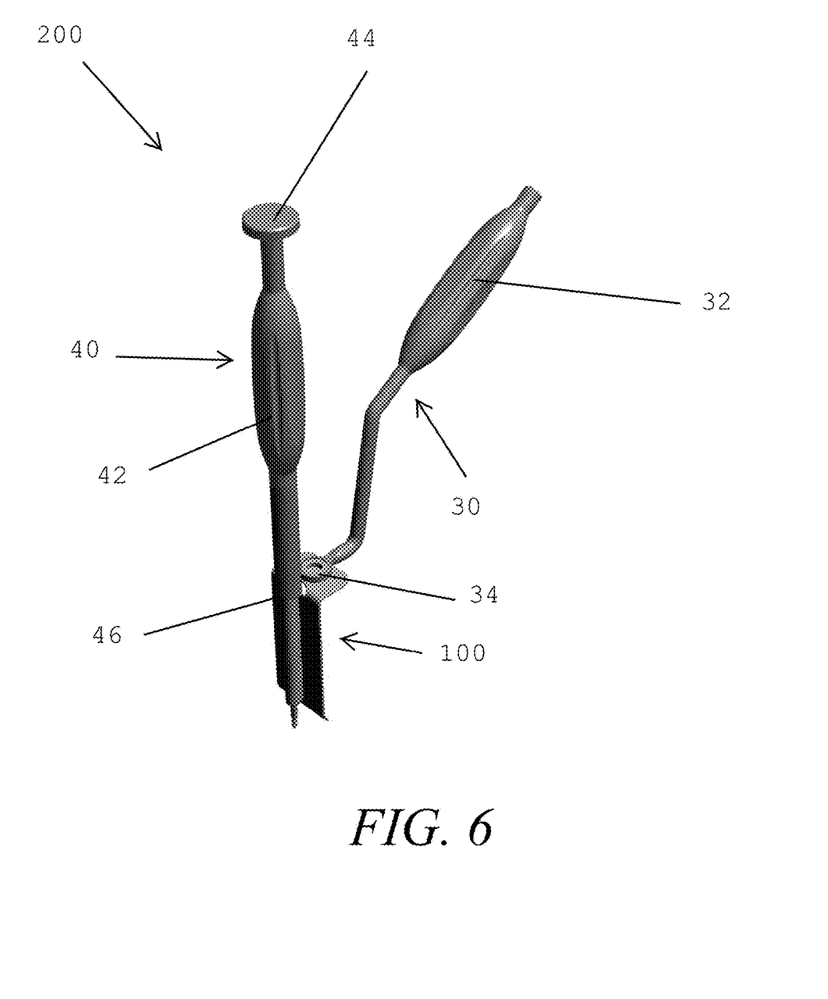
FIG. 6 shows an example retractor system using the example retractor device and an example blade holder tool and screwdriver.

Referring to FIG. 6, the example retractor system 200 includes a retractor device 100 with a blade holder tool 30 and a screw driver 40 provided to support use of the retractor device 100.

Figure 4:
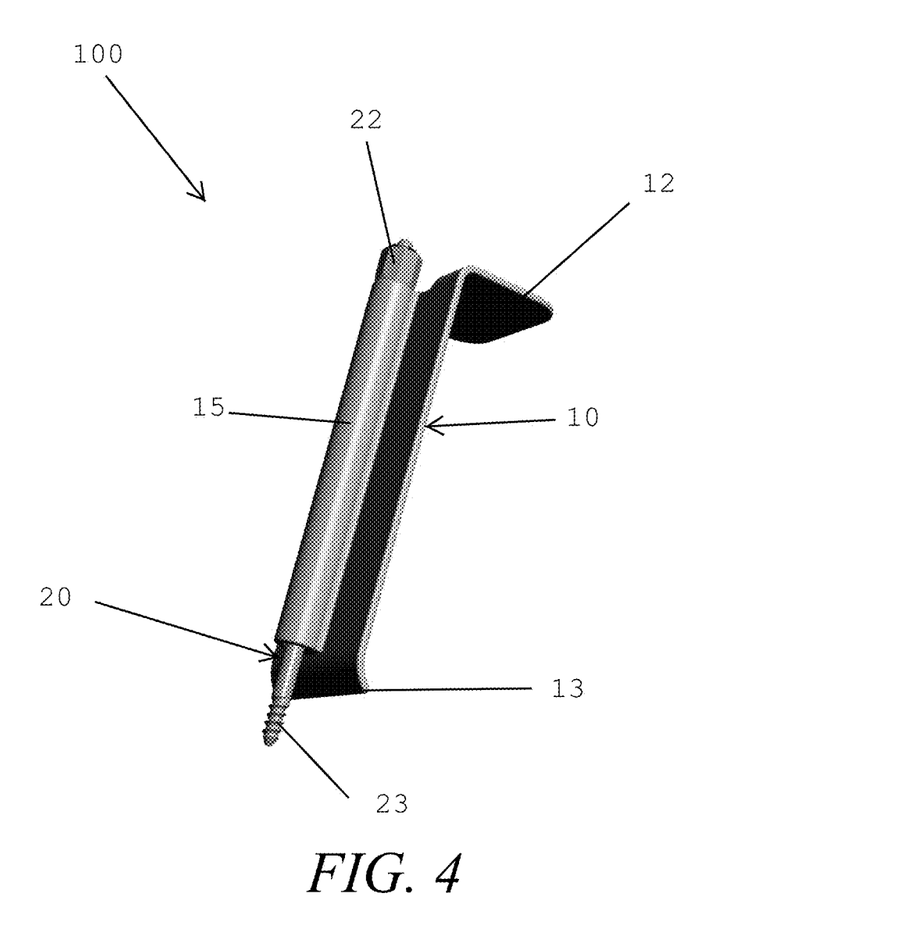
FIGS. 4-5 show different views of an example retractor device using the example vertebral body screw and example smooth retractor blade for use in the example retractor system.
Figure 5:
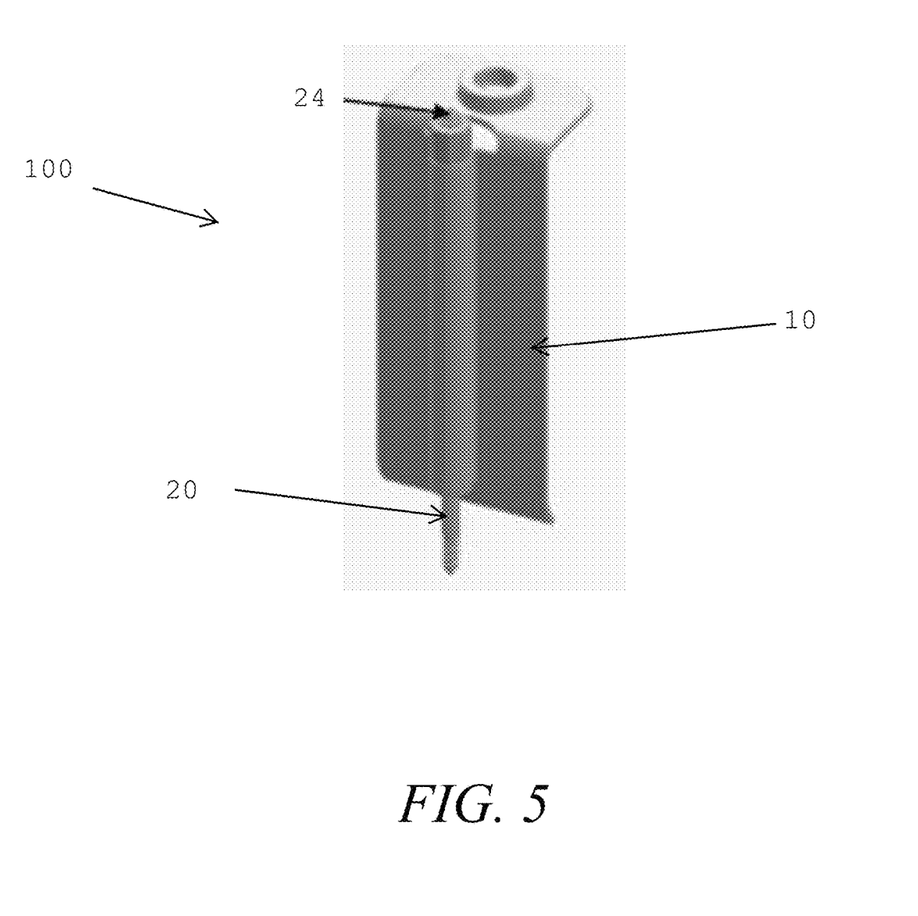

FIGS. 4-5 show different views of the retractor device 100 including a smooth retractor blade 10 and a vertebral body (bone) screw 20.

Figure 1:
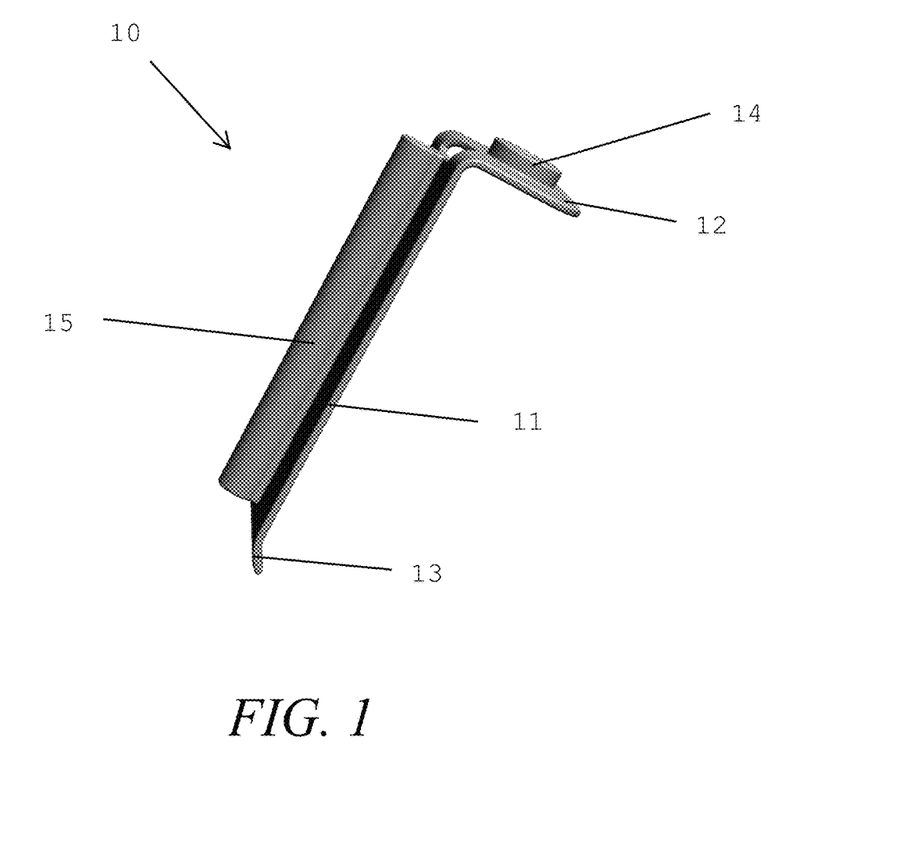
FIGS. 1-2 show different views of an example smooth retractor blade for use in the example retractor system.
Figure 2:
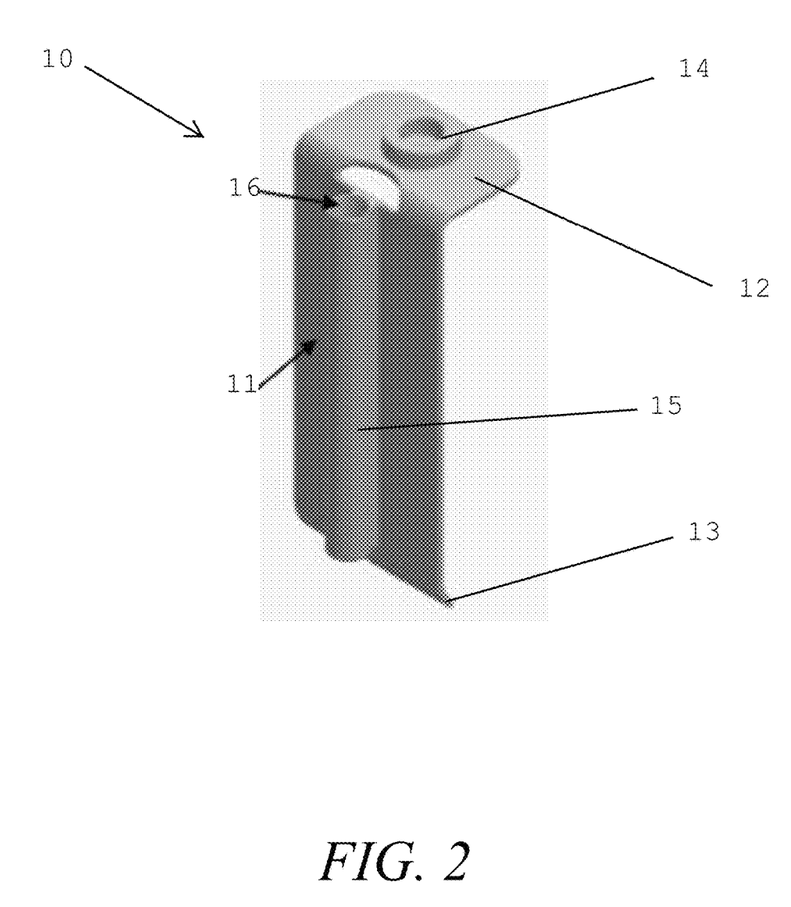
Figure 7:
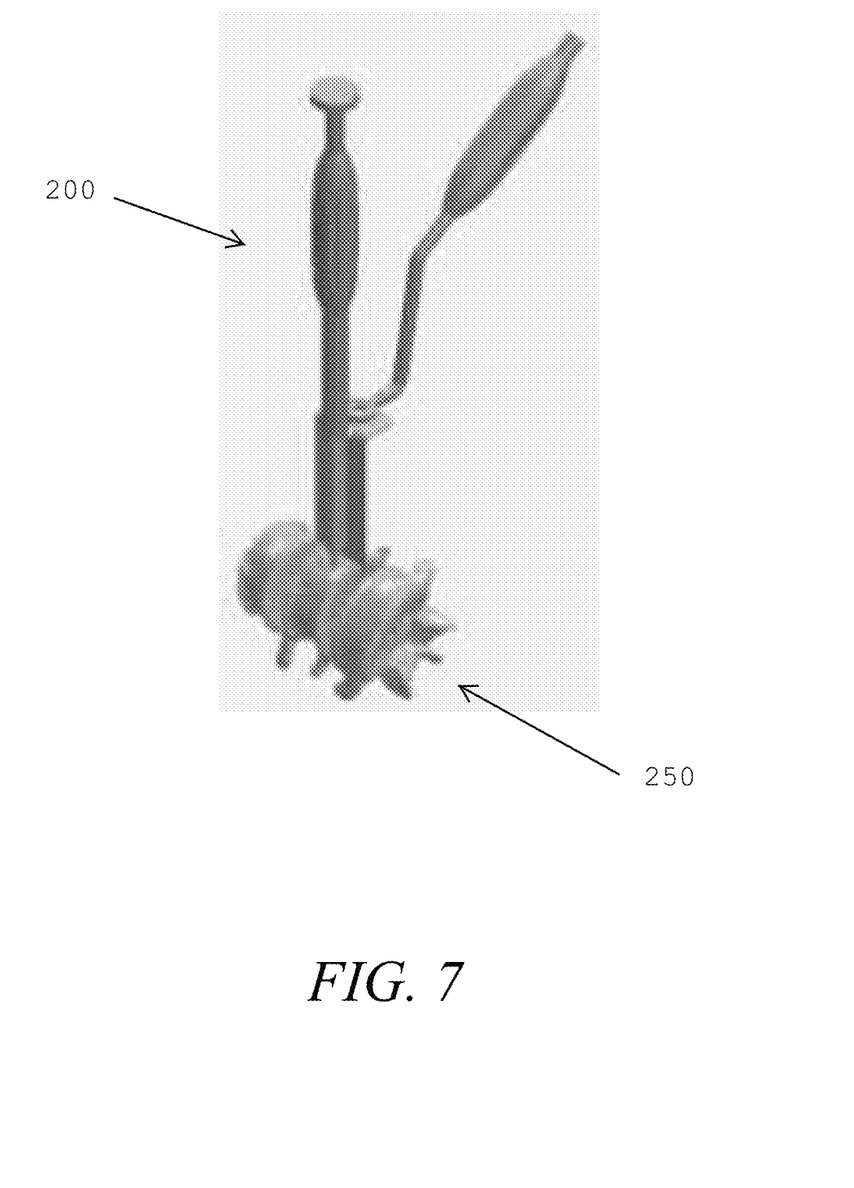
FIG. 7 shows the example retractor system being used in an example surgical procedure.

FIGS. 1-2 show different views of the smooth retractor blade 10 including a horizontal upper platform 12 having a tool connector tab 14 for connecting to the blade holder tool 30, a vertical side body 11 connected to the upper platform 12 and having a screw holder 15 with a channel 16 for receiving the vertebral body screw, and a retractor tab 13 provided at an angle to the vertical side body for interacting with the patient vertebra 250 as shown in FIG. 7. The angle of the retractor tab 13 could be a desired value between 90 and 180 degrees with respect to the vertical side body 11, with a desired angle of about 135 degrees or so being typical.

To construct the retractor blade 10, the upper platform 12, the vertical side body 11, and the retractor tab 13 may be manufactured from a medical grade material, such as a stainless steel, titanium or high strength poly material (PEEK or PEKK), that is formed into the desired shape, for example. Manufacturing techniques could include machining or 3D printing of the base design with secondary operations for the added features required to connect with tools, for example. The tool connector tab 14 may be made separately and welded to the upper platform 12, or it may be integrally machined from the upper platform 12. The screw holder 15 may be formed of a sheet of metal that is formed into a cylinder forming the channel 16, or it may be comprised of a cylindrical piece of material with the channel 16 formed by machining (e.g., drilling) the cylindrical piece.

Figure 3:
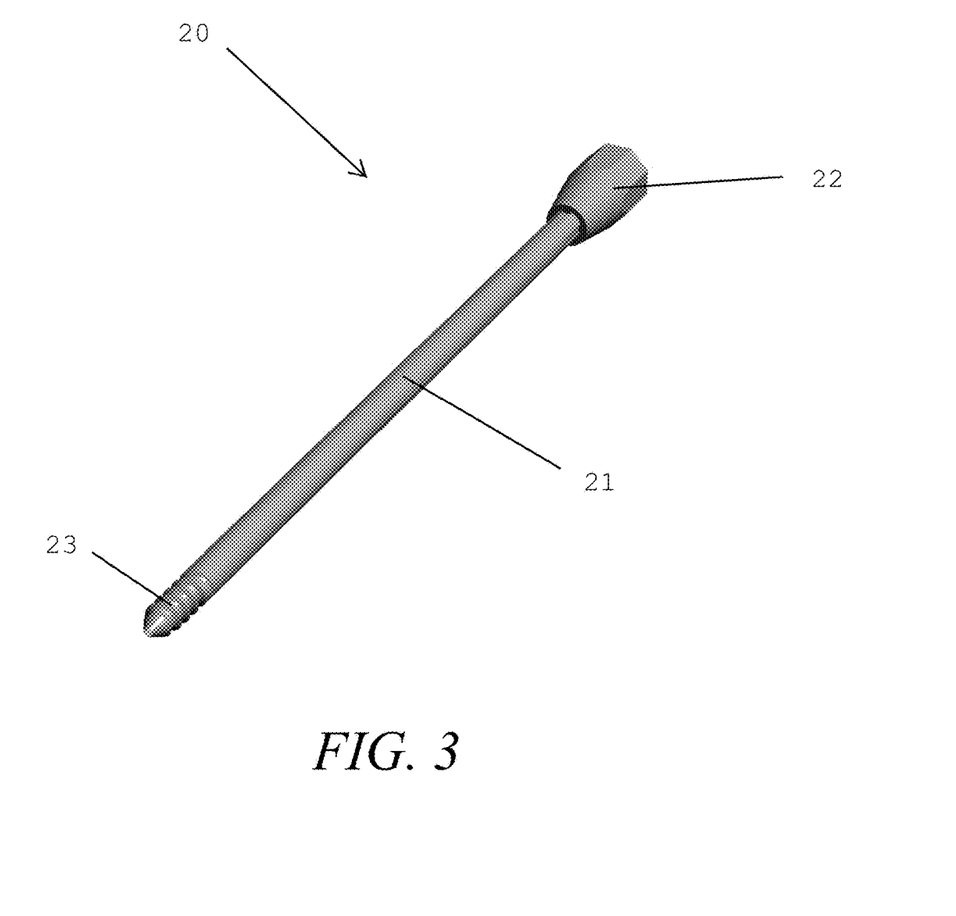
FIG. 3 shows an example vertebral body screw for use in the example retractor system.

FIG. 3 shows the assembled retractor device 100 with the vertebral body screw 20 having a screw head 22, a screw body 21, and screw threads 23 for screwing into the patient vertebra. The vertebral body screw may be formed from any material having sufficient strength to be screwed into bone, such as medical grade stainless steel.

Referring back to FIG. 4, the vertebral body screw 22 is inserted into the channel of screw holder 15 provided on the retractor blade 10 with the threads 23 exiting a bottom of the channel.

The system 200 is further completed as shown in FIG. 6 by adding the screw driver 40 having a handle 32 and an engaging end 46 for engaging the screw head 22. The engaging end 46 will have a female shape corresponding to the male shape of the head 22 shown in FIG. 3. Further added to the system 200 is the blade holder tool 30 having a handle 32 and an engaging end 34 corresponding to the connector tab 14 shown in FIGS. 1-2 for holding the retractor device 100 in place during insertion into the vertebrae 250 of the patient as shown in FIG. 7. The blade holder 30 reliably holds the retractor blade 10 while the retractor blade 10 is being inserted into an incision in the patient, and it holds the retractor device 100 steady while the vertebral body screw 20 is screwed into the vertebrae of the patient.

As an example, the insertion process typically involves the retractor blade 10 being is inserted into an anterior incision in the patient and being positioned with the blade holder tool 30 for protecting soft tissue elements of the patient during an anterior spinal surgical procedure. The vertebral body Screw 20 is then driven through the screw channel 16 provided in the screw holder 15 of the retractor blade 10, with the vertebral body screw 20 being secured to the bone until the anti-rotation face of the screw head 22 bottoms out in the screw channel 16.

The anti-rotation face of the screw head 22 is provided with a roughened surface of a Morse Taper interface to cause a friction forced position hold of the retractor blade.

The blade holder tool 30 can be made of a sufficiently strong material, such as a medical grade stainless steel, with the handle 32 being made of a similar material or a molded plastic or rubber to improve gripping, for example. The blade holder tool 30 is connected to the holder by the engaging end 34 securely connecting to the connector tab 14, and remains secured together until positioned in the body. Such a connection can be provided using a snap feature for mating the engaging end 34 to the connector tab 14. Once the blade is secured by the vertebral body screw 20. the blade is mechanically released from the holder. The screw driver 40 can be constructed of similar materials and may be of a conventional design for bone screws.

Once the procedure is complete and the blade system is to be removed, there are additional features included in the vertebral body screw 20 that can be used to assist the procedure, such as by placing bone wax in the drilled hole. Using the blade holder tool 30 a slight force is placed on the retractor blade 10 to release it from the bone and allow the vertebral body screw 20 to be withdrawn from the bone using the screw driver 40. Prior to engaging the screw driver 40, a bone wax is injected into a cannulated feature 24 of the vertebral body screw 20, as shown in FIG. 5. While the vertebral body screw 20 is being withdrawn, bone wax will fill into the hole caused by the vertebral body screw and prevent bleeding to the external surfaces.

An alternative method to plug the hole created by the vertebral body screw is to use pre-shaped wax plugs that will be manually inserted into the hole in the bone after the vertebral body screw 20 is withdrawn.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A spine retractor system comprising:
a bone screw having a threaded end and a head end;

a screwdriver having a screwdriver handle at one end and an engaging end at another end of the screwdriver away from said screwdriver handle, said engaging end being configured to receive said head end of said bone screw such that said screwdriver is configured to manually drive the bone screw into bone;

a blade holder tool having a handle and a tool end away from said handle; and a retractor blade including:
  a side body,
  a retractor tab provided at an angle at one end of the side body,
  an upper platform provided at another end of the side body, said upper platform being provided at an angle to the side body,
  a tool connector tab provided on a surface of the upper platform, said tool connector tab being configured to be received by the tool end of the blade holder tool such that said blade holder tool securely holds said retractor blade when the tool end receives said tool connector tab, and
  a screw holder provided on a surface of said side body, said screw holder having a channel therethrough, said channel substantially extending along a full length of the side body, to receive the bone screw therethrough,
  wherein the handle of the blade holder tool is angled at an angle less than 90 degrees relative to both the screwdriver and the retractor blade.

2. The spine retractor system of claim 1, wherein said side body, said upper platform, and said retractor tab are formed from a single piece of material.

3. The spine retractor system of claim 1, wherein said tool connector tab is a cylindrical protrusion having a hollow center.

4. The spine retractor system of claim 3, wherein said screw holder is substantially cylindrical and mounted parallel to an axis of said hollow center of the tool connector tab.

5. The spine retractor system of claim 1, wherein said retractor tab is angled away from said screw holder and transitions from said side body as a continuous curve.

6. The spine retractor system of claim 1, wherein said bone screw is configured to contain bone wax.

7. The spine retractor system of claim 1, wherein said retractor blade is comprised of strong medical grade material.

8. The spine retractor system of claim 1, wherein an outer surface of said retractor blade is smoothly finished.

9. The spine retractor system of claim 1, wherein the handle of the blade holder tool comprises a free end configured to be gripped.

10. The spine retractor system of claim 1, wherein the head end comprises a male shape and the engaging end of the screwdriver comprises a female shape corresponding to the male shape of the head end.

11. A spine retractor system comprising:
a bone screw having a threaded end and a head end, said bone screw being configured to contain bone wax;
a screwdriver having a screwdriver handle at one end and an engaging end at another end of the screwdriver away from said screwdriver handle, said engaging end being configured to receive said head end of said bone screw such that said screwdriver is configured to manually drive the bone screw into bone;
a blade holder tool having a handle and a tool end away from said handle; and
a retractor blade including:
  a side body,
  a retractor tab provided at an angle at one end of the side body,
  an upper platform provided at another end of the side body, said upper platform being provided substantially perpendicular to the side body,
  a tool connector tab provided on a surface of the upper platform, said tool connector tab extending from said upper platform and being configured to be received by the tool end of the blade holder tool such that said blade holder tool securely holds said retractor blade when the tool end receives said tool connector tab, wherein said side body, said upper platform, and said retractor tab are formed from a single piece of material with a smoothly finished surface, and
  a substantially cylindrical screw holder provided on a surface of said side body, said screw holder having a channel therethrough, said channel substantially extending along a full length of the side body, to receive the bone screw therethrough,
  wherein the retractor tab is angled away from said screw holder;
  wherein said retractor system is configured to be inserted into an incision in a patient to manually drive the bone screw provided in the channel of the retractor blade into bone while the retractor blade is manually held in place by the blade holder; and
  wherein the handle of the blade holder tool is angled at an angle less than 90 degrees relative to both the screwdriver and the retractor blade.

12. A method of using a spine retractor system according to claim 1, comprising the steps of:
providing the retractor blade;
mating the tool connector tab of the retractor blade with a corresponding portion of the blade holder tool;
manually inserting said retractor blade into an incision in a patient using the blade holder tool;
inserting the bone screw into the channel of the screw holder;
driving the bone screw manually into a portion of a vertebra of the patient using the screwdriver while holding the retractor blade in place using the blade holder tool; and
removing the retractor blade by unscrewing the bone screw and removing the retractor blade from the incision using the blade holder tool.

13. The method of claim 12, further comprising the step of filling a hole formed by the driving step with bone wax.

14. The method of claim 13, wherein said bone wax is obtained from said bone screw.

15. The method of claim 14, wherein said method is performed as part of an anterior spinal surgical procedure.

16. A spine retractor system comprising:
a bone screw having a threaded end and a head end;
a screwdriver having a screwdriver handle at one end and an engaging end at another end of the screwdriver away from said screwdriver handle, said engaging end being configured to receive said head end of said bone screw such that said screwdriver is configured to manually drive the bone screw into bone;
a blade holder tool having a handle and a tool end away from said handle; and
a retractor blade including:
  a side body,
  a retractor tab provided at an angle at one end of the side body, an upper platform provided at another end of the side body, said upper platform being provided at an angle to the side body, a tool connector tab provided on a surface of the upper platform, said tool connector tab being configured to be received by the tool end of the blade holder tool such that said blade holder tool securely holds said retractor blade when the tool end receives said tool connector tab, and a screw holder provided on a surface of said side body, said screw holder having a channel therethrough, said channel substantially extending along a full length of the side body, to receive the bone screw therethrough, wherein the tool connector tab and the tool end are connected by a snap feature for mating the tool end to the connector tab.

* * * * *